(12) United States Patent
Godoy

(10) Patent No.: US 10,947,487 B2
(45) Date of Patent: Mar. 16, 2021

(54) PROCESS FOR THE REUTILIZATION OF YEAST BIOMASS, WITH SEPARATION OF SOLIDS PRIOR TO DISTILLATION AND RECOVERY OF ETHANOL FROM WET CAKE, IN THE INTEGRATION OF ALCOHOLIC FERMENTATIONS OF SUGARCANE AND AMYLACEOUS SUBSTRATES AND/OR FOR AMYLACEOUS-DEDICATED DISTILLERIES

(71) Applicant: FERMENTEC—TECNOLOGIAS EM AÇÚCAR E ÁLCOOL LTDA., Piracicaba (BR)

(72) Inventor: Alexandre Godoy, Piracicaba (BR)

(73) Assignee: FERMENTEC—TECNOLOGIAS EM AÇÚCAR E ÁLCOOL LTDA., Piracicaba (BR)

(*) Notice: Subject to any disclaimer, the term of this patent is extended or adjusted under 35 U.S.C. 154(b) by 399 days.

(21) Appl. No.: 15/933,875

(22) Filed: Mar. 23, 2018

(65) Prior Publication Data
US 2019/0031986 A1    Jan. 31, 2019

(30) Foreign Application Priority Data
Jul. 31, 2017    (BR) .................. 10 2017 016415 2

(51) Int. Cl.
| | | |
|---|---|---|
| C12F 3/06 | (2006.01) | |
| C12G 1/08 | (2006.01) | |
| C12C 7/28 | (2006.01) | |
| C12C 11/02 | (2006.01) | |
| C12C 5/00 | (2006.01) | |
| C12N 1/18 | (2006.01) | |
| C12F 3/08 | (2006.01) | |

(52) U.S. Cl.
CPC .............. *C12F 3/06* (2013.01); *C12C 5/004* (2013.01); *C12C 7/285* (2013.01); *C12C 11/02* (2013.01); *C12F 3/08* (2013.01); *C12G 1/08* (2013.01); *C12N 1/18* (2013.01)

(58) Field of Classification Search
CPC ..... C12F 3/08; C12F 3/06; C12N 1/18; C12C 11/02; C12C 5/004; C12C 7/285; C12G 1/08
USPC .................................... 426/11; 435/161, 261
See application file for complete search history.

(56) References Cited

U.S. PATENT DOCUMENTS

| | | | | |
|---|---|---|---|---|
| 4,617,270 A | * | 10/1986 | Anderson ................ | C12F 3/08 426/11 |
| 5,085,997 A | * | 2/1992 | Muller .................. | C12H 1/063 435/261 |
| 2012/0121565 A1 | * | 5/2012 | Williams ............... | A23K 10/18 424/93.51 |

\* cited by examiner

*Primary Examiner* — Vera Stulii
(74) *Attorney, Agent, or Firm* — Maier & Maier, PLLC

(57) ABSTRACT

A process that provides for the reuse of yeast biomass used in the alcoholic fermentation of both sugarcane and corn in independent or integrated processes with steps of separation and reuse of solids prior to distillation and which are used in the process itself and in other industrial applications such as the production of high protein content (DDG/DDGS) ration, due to the alcohol recovery of the process, biodiesel, cell wall and yeast extract, as well as energy generation. The process also includes a drying step using indirect contact dryers operating with low pressure, non-noble vapors, such as plant vapor and exhaust vapor, and with the recovery of the ethanol contained in the wet cake.

3 Claims, 1 Drawing Sheet

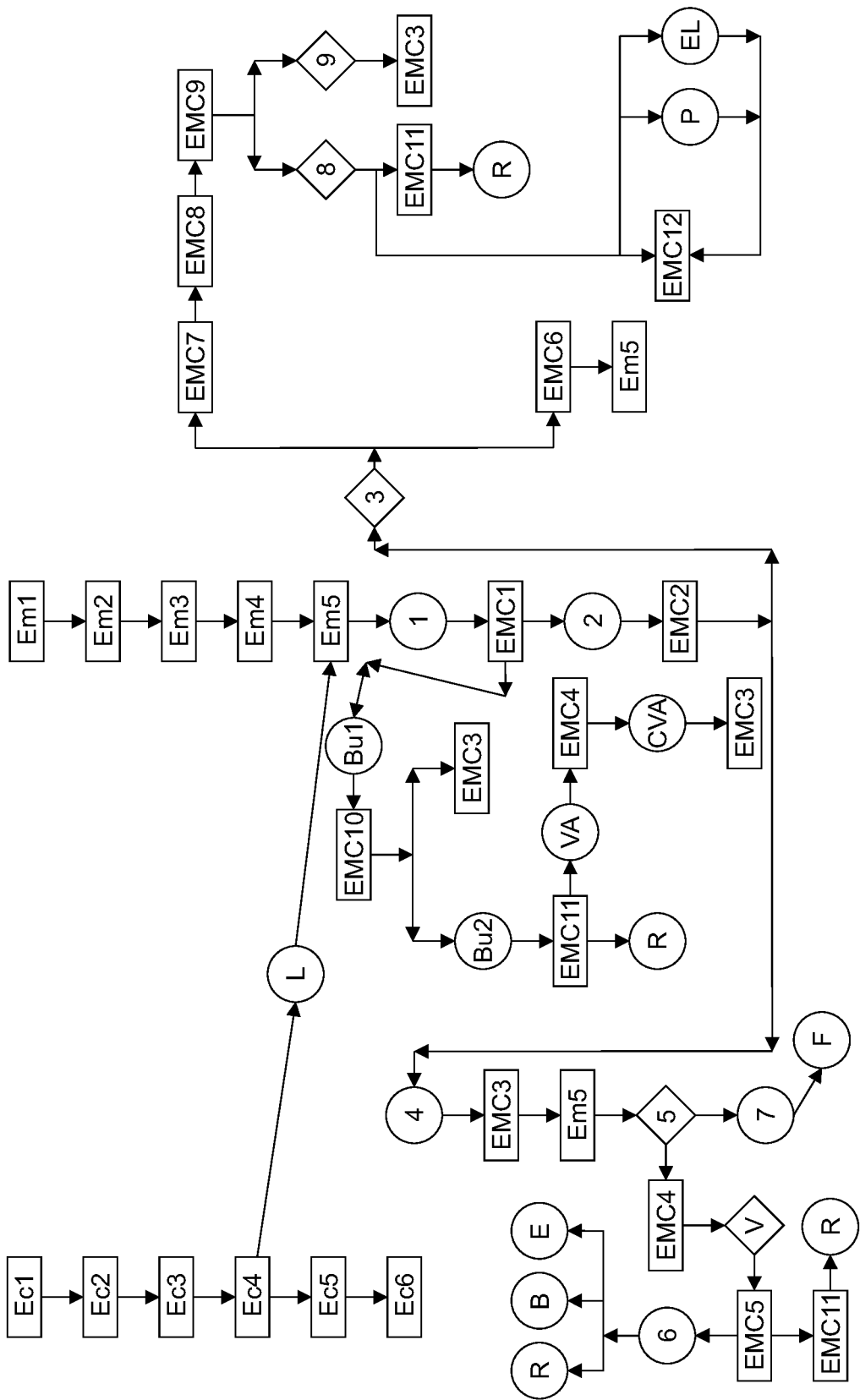

PROCESS FOR THE REUTILIZATION OF YEAST BIOMASS, WITH SEPARATION OF SOLIDS PRIOR TO DISTILLATION AND RECOVERY OF ETHANOL FROM WET CAKE, IN THE INTEGRATION OF ALCOHOLIC FERMENTATIONS OF SUGARCANE AND AMYLACEOUS SUBSTRATES AND/OR FOR AMYLACEOUS-DEDICATED DISTILLERIES

FIELD

This application refers to patents of invention for an unprecedented Process For the Reutilization of Yeast Biomass, With Separation of Solids Prior to Distillation And Recovery of Ethanol from Wet Cake, In The Integration Of Alcoholic Fermentations Of Sugarcane And Amylaceous Substrates And/Or For Amylaceous-Dedicated Distilleries, which refers to a process that provides for the use of yeast discarded in the alcoholic fermentation of sugarcane to be used in the alcoholic fermentations of corn and other starch substrates, thus providing the integration of ethanol production processes from sugarcane and corn, which allows the reduction of corn fermentation time, the correct disposal of a product that would be discarded, as well as the separation of solids before wine distillation and ethanol recovery from the corn wet cake.

The present invention pertains to the field of biotechnology and biochemistry, to the sector of fuel production, obtained from fermentative processes.

BACKGROUND

The use of fossil fuels has been increasingly discouraged by the automobile industry, proof of this is the increased use of flex-fuel engines. With this growing disincentive, the ethanol-producing distilleries have invested in technologies that increase the efficiency of their production and improve their product. In Brazil, most commercialized ethanol is produced with sugar cane, but the use of other substrates, such as corn is also viable and a good alternative to be used not only in the sugarcane harvest, but throughout the year.

For the production of ethanol, yeasts are used for alcoholic fermentation, in which yeasts convert the sugar present in the substrate into cellular energy, to be used in their metabolism, and as a metabolic residue, yeasts produce ethanol and carbon dioxide.

Yeasts used in the alcohol industry have particular characteristics such as fermentation speed, alcohol tolerance, yield and stability. The fermentation rate is determined by the amount of sugar fermented by a quantity of yeast over a period of time.

In most Brazilian distilleries the dehydrated yeast is used as an inoculum, which is usually bought only once in the harvest, according to the quantity needed. This inoculum is propagated until reaching a population of about 8 to 10% (v/v) yeast in the fermenters, and from then on, it is used until the end of the harvest, through its recycling process by the centrifuges.

Conventional corn ethanol production is characterized by being a time consuming and expensive process when compared to the cane ethanol production process. In the conventional corn ethanol production process, 0.01 to 0.05% of dry yeast/$m^3$ of must is inoculated with each new fermentative cycle. This fermentation lasts from 45 to 60 hours and does not reuse yeasts. All the fermented material is sent for distillation and after this step, ethanol, vinasse and a solid material. The solid material is mixed to the concentrated vinasse and then dried to be sold as animal feed, DDG/DDGS ("Distillers Dried Grains"), which is the protein concentrate resulting from the production of corn ethanol.

In Brazil, the production of ethanol from sugarcane is widespread, unlike corn ethanol, because its production is more expensive and time consuming when compared with conventional processes. However, with the reuse of yeast biomass in the integration of both fermentation processes, corn ethanol becomes a good alternative to periods not favorable to sugarcane cultivation and/or processing, since this reuse represents the increase of efficiency in terms of time and costs of corn ethanol production. In addition, a process which provides for the removal of solids after the fermentation step, facilitates and enables the recovery of ethanol and further provides another destination for a by-product; the removal of solids and their use in other steps and/or processes can also be adopted in processes with yeast recycle, both in process integrated with sugarcane, and for distilleries dedicated to starch substrates.

One document of the current state of the art is PI0306523-5, entitled "Process for producing ethanol with immobilized microorganisms in corn cobs and process for immobilizing microorganisms in corn cobs", which refers to a process for immobilizing microorganisms which exempts the use of any reagent; however, in the case of alcoholic yeasts, the concentrated suspension for immobilization is prepared from dry granular ferment or selected strains, thus being a natural process. The use of these immobilized microorganisms naturally aims to make the ethanol production process more efficient, less environmentally impacting and with lower financial costs, objectives that are actually fulfilled, except for the latter, since costs can still be reduced with the reuse of yeasts. In spite of this, the proposed process does not exempt the purchase of dried yeasts every time a new process is initiated, even though it also proposes the use of selected strains, which are more susceptible to contamination by other microorganisms. Thus, it is important to emphasize that fermentation processes by immobilized yeasts are much more susceptible to contamination, either by bacteria or by contaminating yeasts, which weakens the competitiveness of the technology proposed by the aforementioned patent document.

The current state of the art also consists of document PI0806141-6, entitled "Genetically engineered yeast for producing ethanol fuel under stress conditions", which refers to a new genetic construct of yeast with high ethanol productivity in environments whose temperature and acidity are high when compared with conventional yeasts. The use of these genetically modified microorganisms increases the productivity of ethanol, but does not address the reuse of the biomass of these organisms in the fermentation of other substrates, such as corn, since they were specially developed for the fermentation of musts composed of sugarcane. In addition, the use of genetically modified organisms may lead to complications in the disposal of vinasse, since they may be present in the discarded vinasse, which can generate complex environmental problems due to their use in fertigations. On top of that, both the impact that genetically modified yeasts would have on animals using the DDG/DDGS ration from that process and their effect on the health of consumers who ingest meat or milk from animals fed on the DDG/DDGS obtained from this process are unknown.

Thus, from the forgoing and the need for a process that promotes the fermentation of yeast, the use of yeast in the production of ethanol and the use of a by-product in new applications such as new fermentative cycles, production of animal feed with high nutritive content and in energy generation and fertilizer production; the object of the present application is fully consistent with the current scenario.

SUMMARY

The invention aims to provide a process for reusing the yeast biomass used in the fermentation process of sugarcane and/or molasses, in the alcoholic fermentation of starch substrates, preferably in the alcoholic fermentation of corn, and using vinasse, oil and solids for other purposes, for instance, as sources of protein and energy, in fertigation and in the production of biodiesel and animal feed.

The present application relates to a process which provides for the reuse of the yeast biomass used in the alcoholic fermentation of sugarcane and/or molasses in alcoholic fermentations of starch substrates, which provides the integration of the production processes ethanol from sugarcane and corn. Through the reuse of the biomass, the fermentative processes become more efficient, since the use of already active yeasts, coming from the fermentation process of the cane, does not require the preliminary fermentation step, propagation period, in which a good part of the substrate is consumed, the contamination risk is greater, besides being a reasonably slow step, and requiring high amounts of nutrients.

The yeasts used for alcoholic fermentation in the production of ethanol from sugarcane can be reused for other processes of alcoholic fermentation, such as for the ethanol production of starch substrates, such as corn, since it is known that the fermentation process of corn is expensive and time consuming, thus, the reuse of the yeast biomass used in cane fermentation increases the efficiency of the corn ethanol production process. The reuse of the yeasts makes them already active when added to the must, which reduces the fermentation time and the amount of sugar required for the development and activation of the yeasts, which consequently increases their productivity, since the preliminary fermentation step has already been performed.

Increased productivity through rapid fermentation, in addition to increasing daily production, reduces the production cost and the contamination risk by microorganisms that can be harmful. The yield, the ratio between sugar consumed and alcohol produced, must be high, being this essential condition for an industrial yeast.

In addition to increasing productivity in new fermentation processes for ethanol production, the reuse of the yeast makes the DDG/DDGS rations conventionally extracted from the distilled vinasse more nutritious due to the possibility of withdrawing the yeast and the solids before distillation; it also decreases the environmental impact caused by fertigation with vinasse, by reducing its polluting power and, it also allows that in the stops due to lack of cane, as in the rainy periods, the interruption of the industry or even in periods not suitable for the process, the corn ethanol is produced with the reutilized yeast. On top of that, as it is inoculated a lot more yeast with this proposed process, the productivity of the DDG/DDGS ration is, as a consequence, also increased, generating more yield.

The present invention provides the following main advantages:
Reduction of fermenter volume, which reduces installation costs at the distillery;
Dispensing the need for yeast spreaders, reducing installation and operating costs;
There is no sugar consumption from the must to propagate the reutilized yeasts, since they are already active. Once the yeasts are active, they start a new fermentative cycle faster, which reduces the fermentation time in half the current time and reduces bacterial contamination;
Increase of fermentative efficiency between 04 to 10%;
Increase of the amount of yeast in the fermentation of starch substrates, reducing the dependence of the cane fermentation process, even allowing its independence;
Possibility of recovery of the alcohol present in the solid mass withdrawn before the distillation step;
Use of alcohol vapor from the evaporation of water plus ethanol contained in the wet cake as an energy source for the vinasse concentration system.
More nutritive DDG/DDGS rations have a higher protein content than the ration from conventional systems, because they present significantly larger inoculums and are produced with the solid mass withdrawn before distillation, a process that denatures the present proteins;
Reduction of the polluting power of vinasse, due to the reduction of the biological and chemical oxygen demand (BOD and COD) present in the biomass found in the vinasse from the fermentation of the cane juice and/or molasses;
Reduction of distillation campaign time due to withdrawal of solids before the distillation process;
Reduction of equipment and maintenance expenses;
Reduction in nutrient consumption in the propagation of yeast, since part of the vinasse will be recirculated in the liquefaction process, because it is a source of nutrients.

BRIEF DESCRIPTION

The invention will be described in a preferred embodiment, thus, for better understanding, references will be made to the accompanying flowchart.

FIG. 1: Flowchart of the Process for the Reutilization of Yeast Biomass, With Separation of Solids Prior to Distillation And Recovery of Ethanol from the Wet Cake, In The Integration Of Alcoholic Fermentations Of Sugarcane And Amylaceous Substrates And/Or For Amylaceous-Dedicated Distilleries.

DETAILED DESCRIPTION

Both the sugarcane ethanol production process and the corn ethanol production process are known; the process described in the present application integrates the two mentioned production processes as well as proposes steps of solid separation prior to distillation and recovery of ethanol from the wet cake, in processes of reutilization of yeast in the integration of alcoholic fermentations of sugarcane and starch substrates (FIG. 1). The conventional process for producing ethanol from cane is from the known process that begins with the milling of sugarcane (Ec1), which produces a juice, the cane, which is treated (Ec2), pre-evaporated (Ec3) and fermented (Ec4). After fermentation, the mixture is centrifuged (Ec5) and yields the cane wine that is distilled (Ec6). The proposed corn ethanol production process begins with the milling of corn, Dry Milling, (Em1), pre-treatment with the addition of part of the sugarcane vinasse, condensed water and/or flegmass (Em2), this being the first integration of the corn process with the sugarcane, gelatinization, followed by its hydrolysis (Em3) where the corn is cooked and liquefied, then the corn must be cooled (Em4) and the mixture is then added with the enzyme gluco-amylase and fermented (Em5), using yeast (L) treated and coming from the fermentation of the sugarcane, in this step of fermentation of the corn must, where the second integration between the cane/corn processes. Then, the crude wine (1), follows to Decanter centrifugation (EMC1), where it will originate, in one path, the mixture Wine+Yeast+Oil (2), that when leaving the Decanter (EMC1) will be centrifuged in the Sedicanter (EMC2), a centrifuge of fine solids, and will have, in another path, the cream of yeast (3) separated from the mixture by the wine+oil path (4). The wine+oil blend 4 is directed to a flywheel tank (EMC3) and will then be distilled (Em5). The vinasse+oil (5) from this distillation may or may not pass through a vinasse concentrator. If the vinasse passes through this step of concentration (EMC4), which is carried out in multi-effect evaporators commonly used to concentrate vinasse of cane and corn, concentrated vinasse (V) may pass through a separation system of oil through the Tridecanter centrifuge (EMC5), and in the sequence follows to the entrance of the dryer mixed to the moist cake, becoming the DDGS. The oil (6) separated in the Tridecanter (EMC5) is used in the production of ration (R), biodiesel (B) or burned in the boiler (E). If the vinasse does not pass through the concentration system, it will be (7) directed to the field for fertigation (F).

The yeast cream (3), separated in the Sedicanter (EMC2) can be directed to two different routes:
  The yeast treatment step (EMC6), a pre-fermentation, for a period between 1 and 1:30 h can be re-sent to be reused as an inoculum for the fermentation of corn (Em5) thereafter, thus making it so a yeast recycle system;
  It can be sent to an endogenous fermentation tank (EMC7), for a period between 08 and 15 h, at a temperature between 30 and 42° C., where its protein content will increase due to the ethanol recovered from it. After recovery of the ethanol, the yeast is washed (EMC8) with water and centrifuged (EMC9), the solid part of the mixture (8) is added to the wet cake at the inlet of the dryer (EMC11) to yield solids to be used as feed (R), either can be directly dried (EMC12) or can also enter into cell wall (P) and yeast extract (EL) production, these products with high added value and (EMC12). After the liquid part, the alcoholic water (9) is redirected to the flywheel tank where it will be subsequently distilled (EMC3).

In the path out of the Decanter (EMC1), the wet cake (Bu1) proceeds to a filter press (EMC10), providing a 15 to 25% reduction of the moisture of this cake, in order to minimize the consumption of vapor for the drying step (EMC11) from the wet cake in DDGS, as well as the recovery of the permeate with ethanol in the process with the wine to be distilled (EMC3). This "more concentrated" solids cake (Bu2) exiting the filter press (EMC10), goes to the drying step (EMC11), which is caused by the action of indirect contact dryers, unlike the conventional system used, which uses countercurrent hot air to dry the material. The indirect contact dryer operates with low pressure (non-noble) vapors and is usually more readily available in industrial sucroenergy units such as vegetable vapor and exhaust vapor. As there is no direct contact of this vapor with the material being dried, it does not occur the incorporation of water into the system, being possible to recover the vapor condensate (CVA) and its use in thermal regeneration and/or the dilution of process is from corn such as cane. Alcohol vapor (AV) from the evaporation of water+ethanol contained in the wet cake can be used as an energy source for the vinasse concentration system (EMC4) and recovered in the first effect, as well as being simply condensed with water (hull and tube or plates) or even to be used to regenerate heat with another colder source that needs to be heated, being sent to the fly tank (EMC3) to be distilled again (Em5), to recover this ethanol in the process.

When vinasse concentration is reached, its syrup (V) can also be incorporated into the wet cake (Bu2) at the dryer inlet (EMC11), producing the feed.

In the case of distilleries totally dedicated to corn or other starches, that is, not part of sugarcane processing, the process covered by this patent application provides for three possibilities:
  The dedicated distillery may purchase molasses, broth, syrup and/or sugar or other available carbohydrate sources in the market and promote a parallel fermentation, removing the yeast biomass to inoculate in the fermentation of the starch substrate. In this case, the parallel fermentation will function as a "yeast spreader". From the addition of these yeasts to fermentation, the route described above can be followed in order to separate the solids and recover the ethanol.
  If the dedicated corn distillery does not use as a carbohydrate source the sugar cane to propagate the yeast, it can use the corn as its own substrate. Nevertheless, the solids removal process after fermentation and before distillation, described above, can be used, which makes it possible to use the same distillation columns used for sugarcane ethanol, and to benefit from the conditions of producing a DDG/DDGS of higher concentration and quality of proteins.
  The yeast cream, removed from the wine to be distilled, can be resent to the yeast treatment step, and reused as an inoculum for the corn must, thus making it a yeast recycle system.

The invention claimed is:

1. A process for the reutilization of yeast biomass, comprising the steps of:
  a) milling corn to obtain milled corn;
  b) pre-treating the milled corn with sugarcane vinasse, condensed water, and/or flegmass;
  c) hydrolyzing the mixture of step b;
  d) cooling the mixture of step c;
  e) fermenting the mixture of step d using yeast so as to obtain crude wine, the yeast being sourced from prior fermentation;
  f) centrifuging the crude wine so as to obtain a wine+yeast+oil mixture and a wet cake;
  g) centrifuging the wine+yeast+oil mixture so as to obtain cream of yeast and a wine+oil blend; and
  h) distilling the wine+oil blend so as to obtain vinasse+oil;
  i) optionally processing the vinasse+oil according to a first process; and
  j) further processing the cream of yeast according to one or both of a second process and a third process;
  wherein the first process comprises the steps of:
  k) concentrating and separating the vinasse+oil so as to obtain vinasse; and
  l) drying the vinasse with the wet cake so as to obtain DDGS;
  wherein the second process comprises the steps of:
  m) pre-fermenting the cream of yeast; and
  n) utilizing the yeast in step e;
  wherein the third process comprises the steps of:
  o) sending the cream of yeast to an endogenous fermentation tank so as to increase its protein content;
  p) washing and centrifuging the cream of yeast so as to obtain dry yeast;

q) adding the dry yeast to the wet cake used in step l; and/or
r) processing the dry yeast so as to obtain solid animal food and/or obtain cell wall and/or obtain yeast extract.

2. The process of claim 1, further comprising:
pressing the wet cake obtained in step f so as to reduce a moisture content of the wet cake from 25% to 15%, prior to drying the wet cake in step l.

3. The process of claim 1, wherein the drying of step l is performed by at least one indirect contact dryer.

\* \* \* \* \*